(12) United States Patent
Chen et al.

(10) Patent No.: US 11,933,935 B2
(45) Date of Patent: Mar. 19, 2024

(54) METHOD AND SYSTEM FOR DETERMINING GAMMA-RAY MEASUREMENTS USING A SENSITIVITY MAP AND CONTROLLED SAMPLING MOTION

(71) Applicant: ARAMCO SERVICES COMPANY, Houston, TX (US)

(72) Inventors: Jin-Hong Chen, Katy, TX (US); Stacey M. Althaus, Houston, TX (US); Houzhu Zhang, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 212 days.

(21) Appl. No.: 17/455,128

(22) Filed: Nov. 16, 2021

(65) Prior Publication Data
US 2023/0152484 A1    May 18, 2023

(51) Int. Cl.
*G01V 5/12* (2006.01)
*E21B 47/11* (2012.01)
*G01V 5/04* (2006.01)

(52) U.S. Cl.
CPC ............ *G01V 5/12* (2013.01); *E21B 47/111* (2020.05); *G01V 5/045* (2013.01)

(58) Field of Classification Search
CPC .......... G01V 5/045; G01V 5/12; E21B 47/111
See application file for complete search history.

(56) References Cited

U.S. PATENT DOCUMENTS

| 4,464,569 | A | * | 8/1984 | Flaum | G01V 5/102 |
| | | | | | 250/269.6 |
| 4,749,859 | A | * | 6/1988 | Schmidt | G01V 5/101 |
| | | | | | 250/269.8 |
| 4,766,543 | A | * | 8/1988 | Schmidt | G01V 5/06 |
| | | | | | 250/261 |
| 5,282,133 | A | * | 1/1994 | Watson | G01V 5/12 |
| | | | | | 702/11 |

(Continued)

FOREIGN PATENT DOCUMENTS

| CN | 103853929 A | 6/2014 |
| CN | 103913764 A | 7/2014 |
| WO | 2018/116584 A1 | 6/2018 |

OTHER PUBLICATIONS

International Search Report and Written Opinion of the International Searching Authority issued in corresponding International Application No. PCT/US2022/050126, dated Mar. 14, 2023 (15 pages).

(Continued)

*Primary Examiner* — Blake C Riddick
(74) *Attorney, Agent, or Firm* — Osha Bergman Watanabe & Burton LLP

(57) ABSTRACT

A method may include obtaining, using a gamma-ray detector, first acquired gamma-ray data regarding a first core sample. The first acquired gamma-ray data may correspond to various sensor steps. The method may further include determining a sensitivity map based on the first acquired gamma-ray data. The method may further include obtaining, using the gamma-ray detector, second acquired gamma-ray data regarding a second core sample at the sensor steps. The method further includes generating a gamma-ray log using the sensitivity map and a gamma-ray inversion process.

17 Claims, 7 Drawing Sheets

(56) References Cited

U.S. PATENT DOCUMENTS

| | | | | |
|---|---|---|---|---|
| 5,528,029 | A * | 6/1996 | Chapellat | G01V 5/12 250/266 |
| 5,847,398 | A | 12/1998 | Shahar et al. | |
| 6,228,664 | B1 | 5/2001 | Bronson et al. | |
| 2004/0211912 | A1 | 10/2004 | Lightfoot et al. | |
| 2006/0173627 | A1 | 8/2006 | Haugland | |
| 2007/0260403 | A1 * | 11/2007 | Wood | G01V 11/00 702/6 |
| 2008/0156975 | A1 * | 7/2008 | Kieschnick | E21B 25/005 250/255 |
| 2009/0078467 | A1 * | 3/2009 | Castillo | E21B 25/10 175/58 |
| 2009/0248309 | A1 * | 10/2009 | Neville | G01V 5/107 250/269.4 |
| 2010/0004867 | A1 * | 1/2010 | Zhou | G01V 5/12 250/269.3 |
| 2011/0062341 | A1 | 3/2011 | Wever et al. | |
| 2013/0253835 | A1 * | 9/2013 | Whetton | G01V 5/04 702/8 |
| 2014/0214324 | A1 * | 7/2014 | Freedman | G01V 5/10 702/8 |
| 2014/0231639 | A1 * | 8/2014 | O'Connor | G01N 33/24 250/255 |
| 2015/0285943 | A1 * | 10/2015 | Stoller | G01N 33/24 702/8 |
| 2016/0084974 | A1 | 3/2016 | Lerche et al. | |
| 2016/0245934 | A1 | 8/2016 | Shahar et al. | |
| 2016/0313459 | A1 | 10/2016 | Scoullar et al. | |
| 2017/0160425 | A1 * | 6/2017 | Miles | G01V 99/005 |
| 2018/0031732 | A1 * | 2/2018 | Mosse | G01V 99/005 |
| 2018/0136360 | A1 | 5/2018 | Ardjmandpour et al. | |
| 2018/0149768 | A1 | 5/2018 | Guo et al. | |
| 2018/0196160 | A1 * | 7/2018 | Lee | G01V 5/045 |
| 2018/0217073 | A1 * | 8/2018 | Chen | G01V 3/32 |
| 2018/0225868 | A1 * | 8/2018 | Bize | G01V 99/005 |
| 2018/0252101 | A1 * | 9/2018 | Bartetzko | E21B 44/00 |
| 2018/0267199 | A1 * | 9/2018 | Xu | G01V 5/045 |
| 2018/0335546 | A1 * | 11/2018 | Inanc | G01V 5/105 |
| 2019/0064386 | A1 * | 2/2019 | Teague | H01J 35/02 |
| 2020/0033497 | A1 * | 1/2020 | Galford | G01V 5/06 |
| 2020/0158666 | A1 * | 5/2020 | Ashby | G01V 5/125 |
| 2021/0003737 | A1 * | 1/2021 | Whetton | G01V 5/104 |
| 2021/0341640 | A1 * | 11/2021 | Guo | E21B 47/135 |
| 2021/0363874 | A1 * | 11/2021 | Galford | G01V 5/045 |
| 2023/0063340 | A1 * | 3/2023 | Crawford | E21B 49/00 |

OTHER PUBLICATIONS

Farquharson, Colin G. et al., "Non-linear inversion using general measures of data misfit and model structure"; Geophysical Journal International; vol. 134, Issue 1; pp. 213-227; Jul. 1998 (15 pages).

* cited by examiner

METHOD AND SYSTEM FOR DETERMINING GAMMA-RAY MEASUREMENTS USING A SENSITIVITY MAP AND CONTROLLED SAMPLING MOTION

BACKGROUND

A subsurface formation may be analyzed using various measurements obtained through core samples. In particular, core samples may be monitored for detecting various levels of gamma-rays emanating from rock to determine different types of mineral properties and compositions in the formation. However, gamma-ray sensing devices may not provide perfect measurements, as background noise may be measured along with desired gamma-ray signals.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method that includes obtaining, by a computer processor and using a gamma-ray detector, first acquired gamma-ray data regarding a first core sample. The first acquired gamma-ray data corresponds to various sensor steps. The method further includes determining, by the computer processor, a sensitivity map based on the first acquired gamma-ray data. The method further includes obtaining, by the computer processor and using the gamma-ray detector, second acquired gamma-ray data regarding a second core sample at the sensor steps. The method further includes generating, by the computer processor, a gamma-ray log using the sensitivity map and a gamma-ray inversion process.

In general, in one aspect, embodiments relate to a system that includes a gamma-ray detector, and a host device that includes a computer processor. The host device is coupled to the gamma-ray detector. The host device obtains, using the gamma-ray detector, first acquired gamma-ray data regarding a first core sample. The first acquired gamma-ray data corresponds to various sensor steps. The host device determines a sensitivity map based on the first acquired gamma-ray data. The host device obtains, using the gamma-ray detector, second acquired gamma-ray data regarding a second core sample at the sensor steps. The host device generates a gamma-ray log using the sensitivity map and a gamma-ray inversion process.

In general, in one aspect, embodiments relate to a non-transitory computer readable medium storing instructions executable by a computer processor. The instructions obtain, from a gamma-ray detector, first acquired gamma-ray data regarding a first core sample. The first acquired gamma-ray data corresponds to various sensor steps. The instructions determine a sensitivity map based on the first acquired gamma-ray data. The instructions obtain, from the gamma-ray detector, second acquired gamma-ray data regarding a second core sample at the sensor steps. The instructions generate a gamma-ray log using the sensitivity map and a gamma-ray inversion process.

In some embodiments, one or more geological properties are determined for a geological region of interest using a gamma-ray log. The geological region of interest may correspond to a predetermined formation, and the second core sample may be acquired from a well in the predetermined formation. The one or more geological properties may correspond to an amount of shale content in the geological region of interest. In some embodiments a non-linear solver is obtained that performs an iterative reweighted least squares (IRLS) operation. The gamma-ray inversion process may use the nonlinear solver to minimize a predetermined misfit function. In some embodiments, a sensitivity map includes a weighted coefficient for respective sensor step among various sensor steps. The weighted coefficient may determine a filtered gamma-ray signal for a portion of the second acquired gamma-ray data at a respective sensor step. In some embodiment, a first core sample is a baseline core sample. In some embodiments, a gamma-ray detector is moved at various sensor steps along a first axis of the first core sample. The first core sample may be longer with respect to the first axis than a second axis that is perpendicular to the first axis. In some embodiments, the second core sample is acquired from a well in a coring operation using a core bit, a core barrel, and a core catcher. In some embodiments, the gamma-ray detector is a passive detector in a gamma-ray system without an active gamma-ray source. In some embodiments, a logging system is coupled to a wellbore, where the logging system includes a coring tool, and the second core sample is acquired from a well in a coring operation using the coring tool.

In light of the structure and functions described above, embodiments of the invention may include respective means adapted to carry out various steps and functions defined above in accordance with one or more aspects and any one of the embodiments of one or more aspect described herein.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
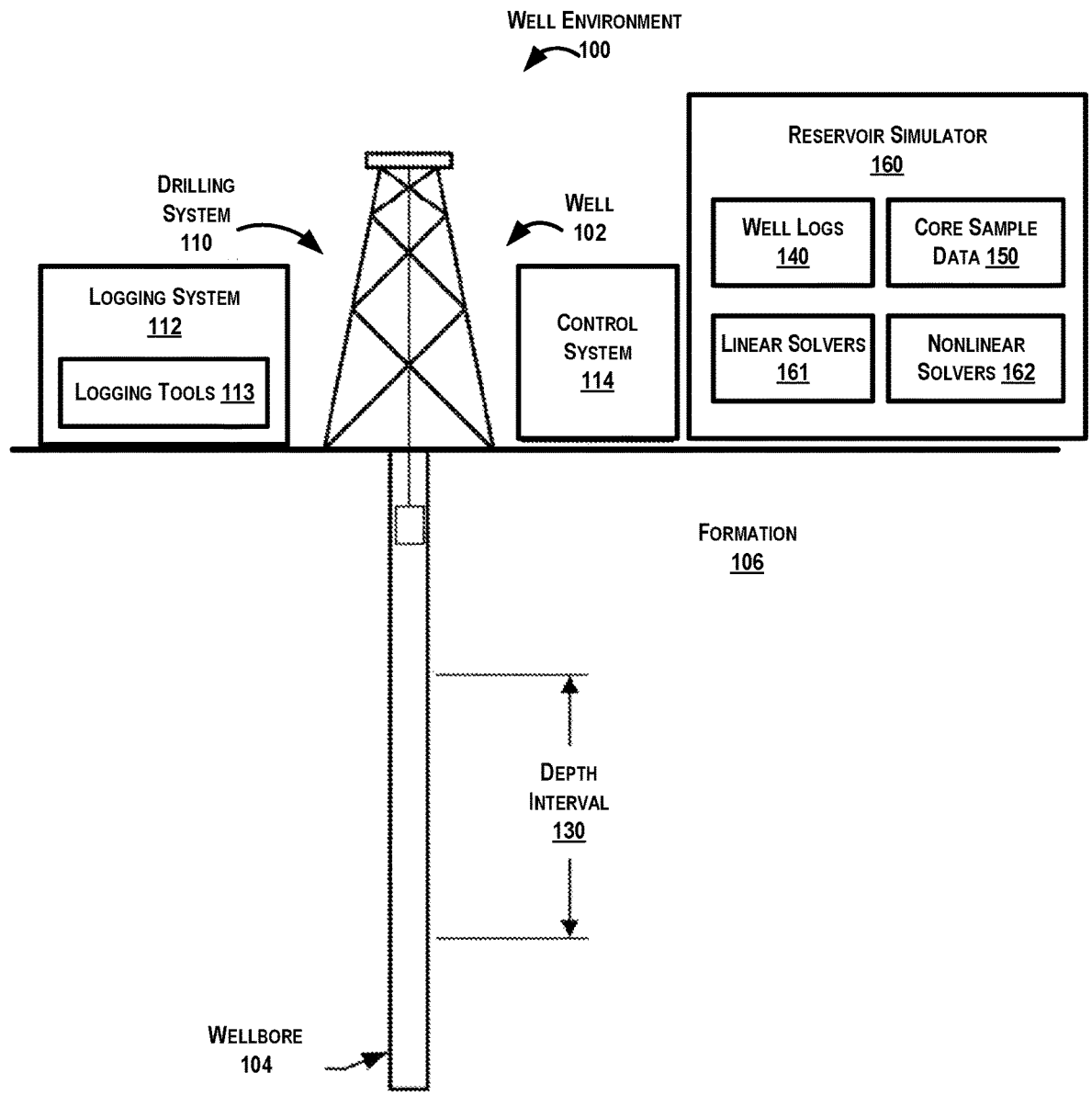
FIGS. 1 and 2 show systems in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology.

Rather, the use of ordinal numbers is to distinguish between the elements. By way of an example, a first element is distinct from a second element, and the first element may encompass more than one element and succeed (or precede) the second element in an ordering of elements.

In general, embodiments of the disclosure include systems and methods for acquiring and/or processing gamma-ray data acquired from one or more core samples. In particular, some embodiments use a data acquisition process that includes a controlled sampling motion to acquire gamma-ray data. In the controlled sampling motion, gamma-ray data may be collected over a series of sensor steps traversing through a sensing region covering a core sample. Thus, each sensor step may define a predetermined change in location or distance of a gamma-ray detector with respect to a core sample within the sensing region. In other words, a core sample from a well or a gamma-ray detector may be moved at periodic intervals through a sensing region to obtain gamma-ray data for each periodic interval.

After performing a data acquisition using a controlled sampling motion, a gamma-ray inversion process may be used to obtain a desired gamma-ray signal from the acquired data. For example, the gamma-inversion process may use a sensitivity map of a gamma-ray system to filter background gamma radiation from the desired gamma-ray signal for each sensor step. The sensitivity map may be based on gamma-ray data acquired using a baseline core sample. The baseline core sample may be a standardizing testing sample with predictable gamma-ray properties that may provide a gamma-ray sensing system with knowledge regarding edge effects from undesired gamma radiation outside a desired gamma-ray detector's aperture. In some embodiments, for example, a sensitivity map is a vector or a series of weighted coefficients to adjusting gamma-ray data at each sensor step. Moreover, the gamma-ray inversion process may use one or more nonlinear solvers to determine a solution for a desired gamma-ray signal from acquired gamma-ray data. Examples of nonlinear solvers includes least squares fitting method, a singular value decomposition (SVD) method, or an iterative reweighted least squares (IRLS) method.

Furthermore, some embodiments may overcome several problems that exist in measuring gamma-rays from a core sample. First, a gamma-ray detector may receive gamma-rays from outside of a desired window (i.e., a portion of a sensing region) can also be detected. Thus, a gamma-ray measurement may not accurately match describe a specific portion of a core sample undergoing analysis. When a gamma-ray log is acquired along an axis of a core sample, various edge effects may be included in the gamma-ray data and thereby reduce the accuracy of a desired gamma-ray signal being measured. Secondly, certain types of core samples may require a spatial sensor resolution unavailable with some detector apertures. For example, some gamma-ray sensing systems may acquire poor measurements regarding thinly laminated core samples. Thus, some embodiments may overcome one or more technological problems associated with gamma-ray detection in core samples.

Turning to FIG. 1, FIG. 1 shows a schematic diagram in accordance with one or more embodiments. As shown, FIG. 1 illustrates a well environment (100) that may include a well (102) having a wellbore (104) extending into a formation (106). The wellbore (104) may include a bored hole that extends from the surface into a target zone of the formation (106), such as a reservoir. The formation (106) may include various formation characteristics of interest, such as formation porosity, formation permeability, resistivity, density, water saturation, and the like. Porosity may indicate how much space exists in a particular rock within an area of interest in the formation (106), where oil, gas, and/or water may be trapped. Permeability may indicate the ability of liquids and gases to flow through the rock within the area of interest. Resistivity may indicate how strongly rock and/or fluid within the formation (106) opposes the flow of electrical current. For example, resistivity may be indicative of the porosity of the formation (106) and the presence of hydrocarbons. More specifically, resistivity may be relatively low for a formation that has high porosity and a large amount of water, and resistivity may be relatively high for a formation that has low porosity or includes a large amount of hydrocarbons. Water saturation may indicate the fraction of water in a given pore space.

Keeping with FIG. 1, the well environment (100) may include a reservoir simulator (160) and various well systems, such as a drilling system (110), a logging system (112), a control system (114), and a well completion system (not shown). The drilling system (110) may include a drill string, drill bit, a mud circulation system and/or the like for use in boring the wellbore (104) into the formation (106). The control system (114) may include hardware and/or software for managing drilling operations and/or maintenance operations. For example, the control system (114) may include one or more programmable logic controllers (PLCs) that include hardware and/or software with functionality to control one or more processes performed by the drilling system (110). Specifically, a programmable logic controller may control valve states, fluid levels, pipe pressures, warning alarms, and/or pressure releases throughout a drilling rig. In particular, a programmable logic controller may be a ruggedized computer system with functionality to withstand vibrations, extreme temperatures, wet conditions, and/or dusty conditions, for example, around a drilling rig. Without loss of generality, the term "control system" may refer to a drilling operation control system that is used to operate and control the equipment, a data acquisition and monitoring system that is used to acquire equipment data and to monitor one or more well operations, or a well interpretation software system that is used to analyze and understand well events, such as drilling progress. A logging system may be similar to a control system with a specific focus on managing one or more logging tools.

Turning to the reservoir simulator (160), a reservoir simulator (160) may include hardware and/or software with functionality for storing and/or analyzing well logs (140), core sample data (150), seismic data, and/or other types of data to determine reservoir properties regarding one or more geological regions. While the reservoir simulator (160) is shown at a well site, in some embodiments, the reservoir simulator (160) may be remote from a well site. In some embodiments, the reservoir simulator (160) is implemented as part of a software platform for the control system (114). The software platform may obtain data acquired by the drilling system (110) and logging system (112) as inputs, which may include multiple data types from multiple sources. The software platform may aggregate the data from these systems (110, 112) in real time for rapid analysis. In some embodiments, the control system (114), the logging system (112), the reservoir simulator (160), and/or a user device coupled to one of these systems may include a computer system that is similar to the computer system (702) described below with regard to FIG. 7 and the accompanying description.

In some embodiments, a reservoir simulator includes one or more linear solvers (e.g., linear solvers (161)) and/or one or more nonlinear solvers (e.g., nonlinear solvers (162)) to perform various data processing operations. In particular, a linear solver or a nonlinear solver may include hardware and/or software that perform mathematical operations in order to determine a solution to a predetermined data analysis problem. For example, a solver may be arbitrarily nested (i.e., as a "nested solver") within an inversion workflow (e.g., a gamma-ray inversion process) that determines individual property values of one or more linear equations (e.g., values within a single grid or multiple grids) or one or more nonlinear equations.

With respect to nonlinear equations, a nonlinear solver may determine a solution to a nonlinear system, in which a change of an output is not proportional to a change of an input to the nonlinear system. As such, a nonlinear solver may be an iterative solver that implements a repeating algorithmic procedure that includes one or more predetermined termination criteria (e.g., when a particular criterion is satisfied based on an updated value, the iterative method may terminate). Likewise, an iterative solver may use a search method, such as a Newton-Raphson method (also called "Newton's method"), a secant method, or a bisection method, to determine a solution to a particular problem or equation. For example, a Newton-Raphson method may include a root-finding algorithm that produces successively better approximations to the roots of a real-valued function. A secant method may include a root-finding algorithm that uses a succession of roots of secant lines to better approximate a root of a real-valued function. A bisection method (also called a "binary search method") may include a root-finding algorithm applicable to various continuous functions that has two known values with opposite signs. The bisection method may repeatedly bisect an interval defined by these known values and then select a subinterval in which a continuous function changes signs (i.e., that contains a root).

The logging system (112) may include one or more logging tools (113) for use in generating well logs of the formation (106). For example, a logging tool may be lowered into the wellbore (104) to acquire measurements as the tool traverses a depth interval (130) (e.g., a targeted reservoir section) of the wellbore (104). The plot of the logging measurements versus depth may be referred to as a "well log". Well logs (140) may provide depth measurements of the well (104) that describe such reservoir characteristics as formation porosity, formation permeability, resistivity, water saturation, and the like. The resulting logging measurements may be stored and/or processed, for example, by the control system (114), to generate corresponding well logs for the well (102). A well log (140) may include, for example, a plot of a logging response time versus true vertical depth (TVD) across the depth interval (130) of the wellbore (104).

Turning to examples of logging techniques, multiple types of logging techniques are available for determining various reservoir characteristics. In some embodiments, gamma ray logging is used to measure naturally occurring gamma radiation to characterize rock or sediment regions within a wellbore. In particular, different types of rock may emit different amounts and different spectra of natural gamma radiation. More specifically, gamma-rays may include electromagnetic radiation from atomic nuclei of an unstable element during a spontaneous decay, such as found in potassium (K), uranium (U), and thorium (Th). Different radioactive materials emits gamma rays with different energy levels, where measurement of natural gamma rays may have many important applications downhole. For example, gamma ray logs may distinguish between shales and sandstones/carbonate rocks because radioactive potassium may be common to shales. Likewise, the cation exchange capacity of clay within shales may also result in higher absorption of uranium and thorium further increasing the amount of gamma radiation produced by shales.

Keeping with gamma-ray logging techniques, some embodiments use passive gamma-ray devices for detecting gamma-rays. For example, a measurement system may include no active gamma-ray source and only a single passive detector. Examples of gamma-ray detectors include gross gamma ray counters, spectral devices, and gamma-ray sondes. In particular, a gamma-ray sonde may be a gamma-ray logging tool that records a total flux of gamma radiation integrated over multiple energies emanating from a formation as a single count rate in order to produce a gamma ray curve. However, many physical parameters of a detector device may affect which gamma rays are sensed by a specific gamma-ray detector. Because many gamma rays may pass through a gamma-ray detector with no effect, relevant physical parameters may include a size and thickness of a detector, an angle that it subtends, and its material composition. Likewise, a detector's housing, a casing, and even density of borehole fluid may filter gamma rays coming from a formation or individual core samples.

Turning to coring, reservoir characteristics may be determined using core sample data (e.g., core sample data (150)) acquired from a well site. For example, certain reservoir characteristics can be determined via coring (e.g., physical extraction of rock specimens) to produce core specimens and/or logging operations (e.g., wireline logging, logging-while-drilling (LWD) and measurement-while-drilling (MWD)). Coring operations may include physically extracting a rock specimen from a region of interest within the wellbore (104) for detailed laboratory analysis. For example, when drilling an oil or gas well, a coring bit may cut core plugs (or "cores" or "core specimens" or "core samples") from the formation (106) and bring the core plugs to the surface, and these core specimens may be analyzed at the surface (e.g., in a lab) to determine various characteristics of the formation (106) at the location where the specimen was obtained. In some embodiments, natural gamma rays are also routinely measured on acquired core samples, such as for depth matching with borehole gamma-ray logs and for correlation with other accurate high-spatial-resolution (HSR) studies on the cores (e.g., computerized tomography (CT), nuclear magnetic resonance (NMR), and X-ray fluorescence (XRF)).

Turning to various coring technique examples, conventional coring may include collecting a cylindrical specimen of rock from the wellbore (104) using a core bit, a core barrel, and a core catcher. The core bit may have a hole in its center that allows the core bit to drill around a central cylinder of rock. Subsequently, the resulting core specimen may be acquired by the core bit and disposed inside the core barrel. More specifically, the core barrel may include a special storage chamber within a coring tool for holding the core specimen. Furthermore, the core catcher may provide a grip to the bottom of a core and, as tension is applied to the drill string, the rock under the core breaks away from the undrilled formation below coring tool. Thus, the core catcher may retain the core specimen to avoid the core specimen falling through the bottom of the drill string.

Keeping with FIG. 1, geosteering may be used to position the drill bit or drill string of the drilling system (110) relative to a boundary between different subsurface layers (e.g., overlying, underlying, and lateral layers of a pay zone) during drilling operations. In particular, a control system (114) may communicate geosteering commands to the drilling system (110) based on well log data updates that are further adjusted by the reservoir simulator (160). As such, the control system (114) may generate one or more control signals for drilling equipment (or a logging system may generate for logging equipment) based on an updated well path design. As such, a geosteering system may use various sensors located inside or adjacent to the drill string to determine different rock formations within a well path. In some geosteering systems, drilling tools may use resistivity or acoustic measurements to guide the drill bit during horizontal or lateral drilling.

Figure 2:
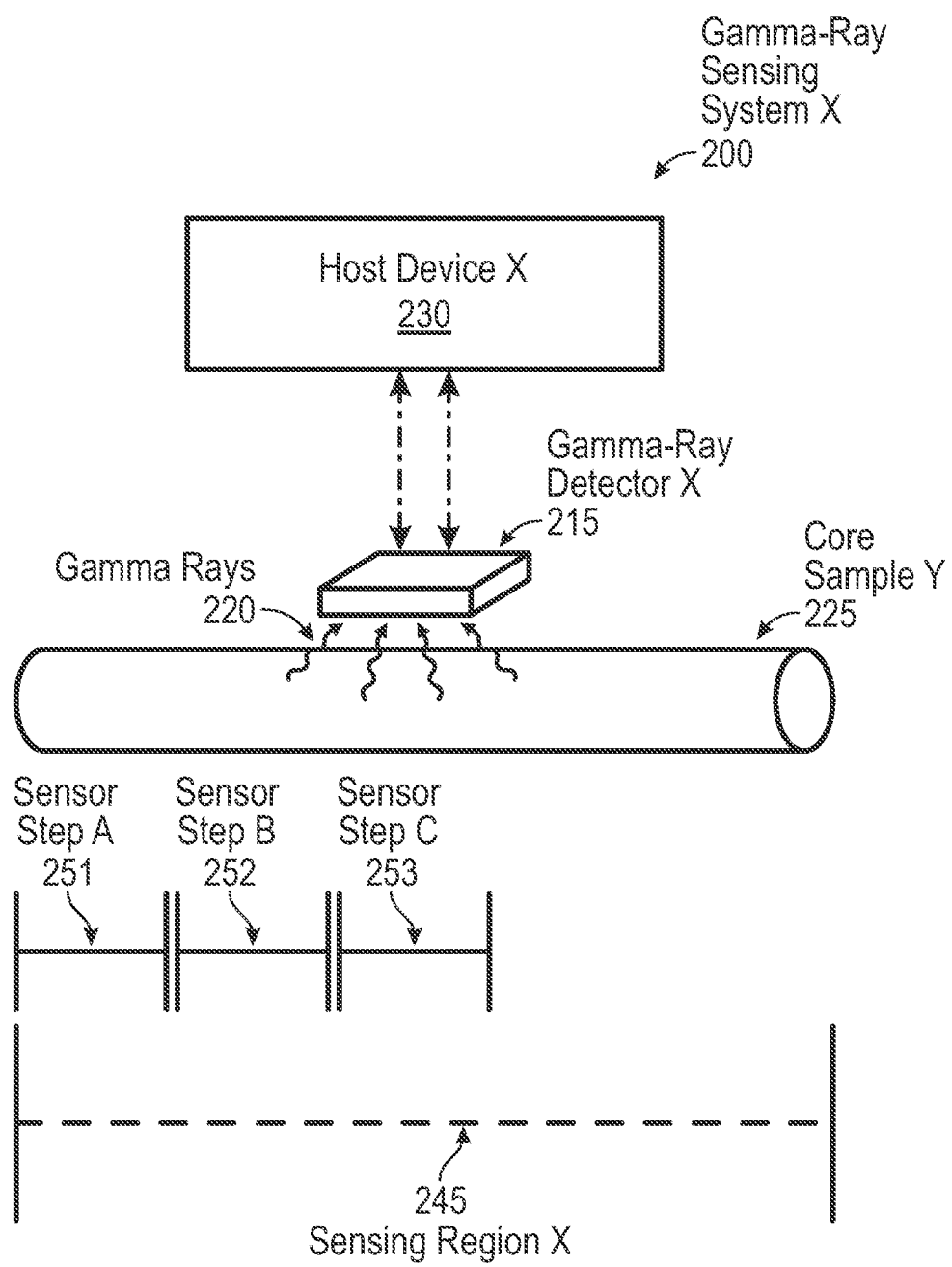

Turning to FIG. 2, FIG. 2 shows a schematic diagram in accordance with one or more embodiments. In FIG. 2, a gamma-ray sensing system (e.g., gamma-ray sensing system X (200)) may include one or more gamma-ray detectors (e.g., gamma-ray detector X (215)), a core sample (e.g., core sample Y (225)), and/or a host device (e.g., host device X (230)) coupled to the one or more gamma-ray detectors. For example, the gamma-ray detector X (215) may be a passive gamma-ray detector that measures gamma rays (220). A gamma-ray sensing system may thereby acquire various measurements of natural gamma-ray radiation at a predetermined distance (e.g., within a few inches) from a core sample in order to measure emitted gamma-rays from different sections of the core sample. A host device may be a computer system similar to computer system (702) in FIG. 7 below that performs various data processing on acquired gamma-ray data (such as gamma-ray inversion operations or determining sensitivity maps). Likewise, a one-dimensional (1D) core gamma-ray log may be generated by moving a core sample in a controlled sampling motion with respect to the gamma-ray detector from one end of a sensing region (e.g., sensing region X (245)) to the other end of the sensing region. In some embodiments, a sensing region is divided into multiple sensor steps (e.g., sensor step A (251), sensor step B (252), sensor step C (253)) that correspond to different measurement intervals within a data acquisition process. Thus, different portions of acquired gamma ray data may correspond to different sensor steps within a sensing region.

Furthermore, gamma-ray may be measured along a major axis of a core sample (i.e., an axis corresponding to the longest dimension of a core sample). As shown in FIG. 2, the major axis of core sample Y (225) is a horizontal axis. However, a gamma-ray sensing system may also acquire gamma-ray data along a minor axis, such as depth dependent gamma ray measurements along a depth axis of a core sample. For example, the depth axis may be perpendicular to the major axis in a gamma-ray sensing system. With respect to gamma-ray sensing system X (200), a long core is pushed through the sensing region X (245), while the gamma-ray detector X (215) detect gamma rays (220) at a given section (or sensor step) of the core sample Y (225). Thus, a gamma-ray sensing system X (200) may obtain a one-dimensional real distribution of gamma-ray measurements along the core sample Y (225).

While FIGS. 1 and 2 shows various configurations of components, other configurations may be used without departing from the scope of the disclosure. For example, various components in FIGS. 1 and 2 may be combined to create a single component. As another example, the functionality performed by a single component may be performed by two or more components.

Figure 3:
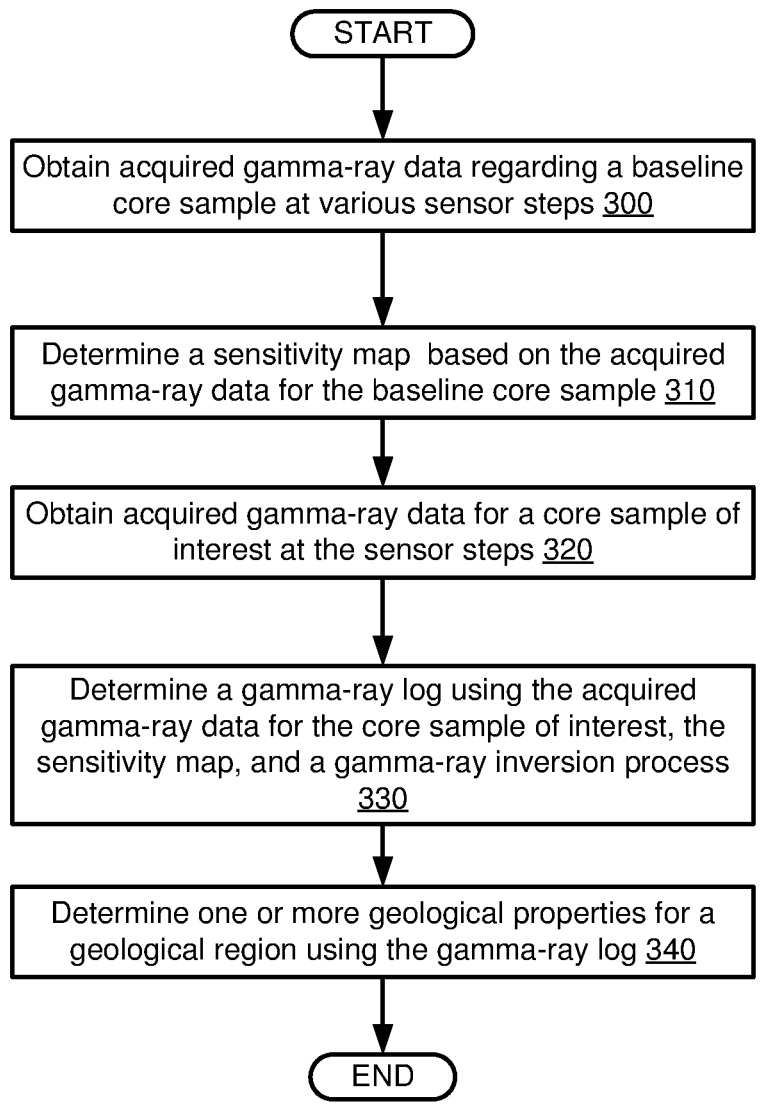
FIG. 3 shows a flowchart in accordance with one or more embodiments.

Turning to FIG. 3, FIG. 3 shows a flowchart in accordance with one or more embodiments. Specifically, FIG. 3 describes a general method for determining gamma-ray data for a core sample. One or more blocks in FIG. 3 may be performed by one or more components (e.g., gamma-ray sensing system X (200)) as described in FIGS. 1 and/or 2. While the various blocks in FIG. 3 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 300, acquired gamma-ray data are obtained regarding a baseline core sample at various sensor steps in accordance with one or more embodiments. In some embodiments, the baseline core sample is a standard sample that is selected with a predetermined size equal to a desired sensor resolution. For example, the baseline core sample may be made of a particular material with identifiable levels of gamma-ray emissions. The length of the baseline core sample may also be selected to match a similar length as a core sample of interest, e.g., a core sample from a well that is undergoing analysis. Accordingly, a sensitivity map of a gamma-ray sensing system may be determined using the acquired gamma-ray data from the baseline core sample (e.g., in Block 310 below). In some embodiments, a baseline core sample is not a core sample, but a configured specimen used to obtain various properties of a gamma-ray sensing system. The baseline core sample may contain, for example, known quantities of elements generally found in a natural rock samples, such as specific amounts of potassium, uranium, and/or thorium.

Moreover, acquired gamma-ray data may be obtained for a baseline core sample using a controlled sampling motion similar to the data acquisition process for a core sample of interest. For example, a desired sensor resolution for a core sample of interest may determine both a size of a baseline core sample and the size of sensor steps within the controlled sampling motion.

In Block 310, a sensitivity map is determined based on acquired gamma-ray data for a baseline core sample in accordance with one or more embodiments. In particular, a sensitivity map may be obtained from various acquired gamma-ray intensities by moving the baseline core sample along a gamma-ray detector in a step-by-step manner in accordance with a desired sensor resolution (such as a spatial resolution). The resulting sensitivity map for a gamma-ray sensing system may be specific to a particular type of gamma-ray detector (e.g., number of gamma-ray detectors or the shape/size of core sample of interest). Likewise, the resulting sensitivity map may also be defined with respect to any core samples of interest that will be later analyzed by a gamma-ray sensing system. As such, the resulting sensitivity map may be a series of coefficients (such as weighted coefficients), values defined in a vector or matrix, one or more curves, or a predetermined function. Likewise, the resulting sensitivity map may be defined as a table associating different sensor steps with different response values in acquired gamma-ray data.

Figure 4:
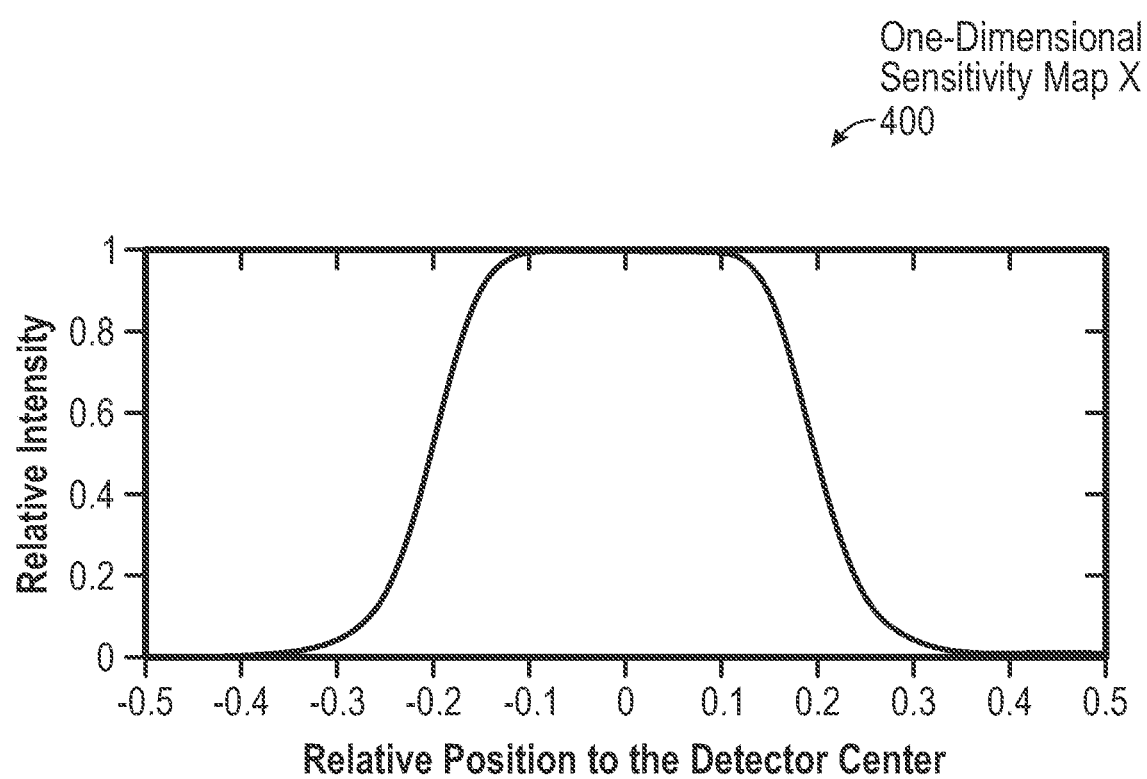
FIGS. 4, 5, and 6 show examples in accordance with one or more embodiments.

Turning to FIG. 4, FIG. 4 shows an example of a one-dimensional sensitivity map X (400) of a gamma-ray sensing system. The one-dimensional sensitivity map X (400) has a spatial resolution for a gamma-ray sensing system based on a particular detector's aperture. However, as shown in FIG. 4, the one-dimensional sensitivity map X (400) may be unable to resolve thinly laminated core samples because of this spatial resolution. In some embodiments, a sensitivity map is configured based on adjusting the size of sensor steps, core sample dimensions, desired spatial resolution, and/or one or more gamma-ray detector properties. Thus, sensor steps may be configured to achieve a sensitivity map that can optimize a gamma-ray inversion process, such as by minimizing various edge effects from unwanted gamma-rays in a sensing region.

Returning to FIG. 3, in Block 320, acquired gamma-ray data is obtained for a core sample of interest at various sensor steps in accordance with one or more embodiments. The core sample of interest may obtained from a well in a formation selected for further analysis, e.g., for determining a location of hydrocarbons or a place for a stimulation treatment. For example, a core sample of interest may be acquired using a coring operation described above in FIG. 1 and the accompanying description. Moreover, acquired gamma-ray data may be obtained from a gamma-ray sensing system where multiple gamma-ray measurements are acquired in a controlled sampling manner by moving a core sample in a step-wise fashion along a gamma-ray detector. After each sensor step, for example, a gamma-ray data acquisition is made to produce a series of gamma-ray measurements. For example, the data acquisition process may begin with a top of a core against the start of a sensitive region or sensing window of the gamma-ray sensing system. Thus, acquired gamma-ray data in an initial sensor step may be a largely background signal. While moving the core sample of interest with additional sensor steps, gamma-ray data may be acquired along an entire length of the core sample. The data acquisition process may continue until the core sample completely passes along the sensing region. Thus, acquired game-ray data in a final sensor step may once again result in a detector signal that is largely background noise.

Figure 5:
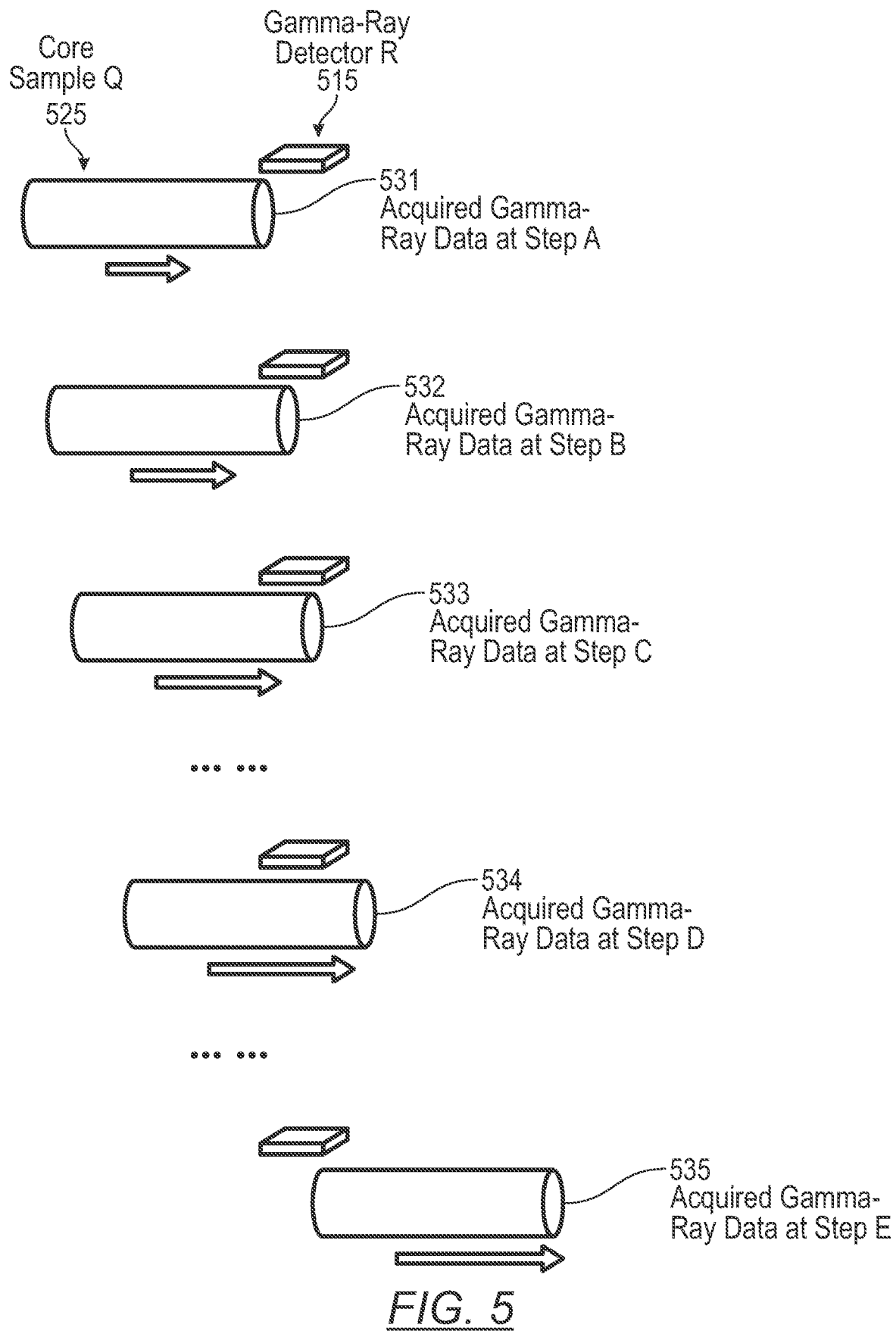

Turning to FIG. 5, FIG. 5 illustrates a gamma-ray data acquisition process in accordance with one or more embodiments. As shown in FIG. 5, FIG. 5 illustrates a core sample Q (525) that is moved in a step-by-step manner passing a gamma-ray detector R (515). At each sensor step, acquired gamma ray data is obtained from detected gamma-ray signals, i.e., acquired gamma ray data at step A (531), acquired gamma ray data at step B (532), acquired gamma ray data at step C (533), acquired gamma ray data at step D (534), and acquired gamma ray data at step E (535). As such, the gamma-ray data acquisition process in FIG. 5 results in a gamma-ray distribution based on multiple positions of the core sample Q (525) with respect to the gamma-ray detector R (515).

Returning to FIG. 2, in Block 330, a gamma-ray log is determined using acquired gamma-ray data for a core sample of interest, a sensitivity map, and a gamma-ray inversion process in accordance with one or more embodiments. After acquiring gamma-ray data using multiple sensor steps, one or more gamma-ray inversion processes may be used to determine a gamma-ray log that describes the core sample of interest. The result of the gamma-ray inversion process may be filtered gamma-ray data with a desired gamma-ray signal and reduced gamma-ray noise. By using a sensitivity map, for example, desired gamma-ray signals may be filtered from background gamma-ray noise within the acquired gamma-ray data. In some embodiments, acquired gamma ray data may be expressed using the following equation:

$$s_i = r_1 a_i + r_2 a_{i-1} + r_3 a_{i-2} + r_4 a_{i-3} + \ldots + r_n a_{i-n+1} \qquad \text{Equation (1)}$$

where i corresponds to a particular sensor step, $s_i$ is a detected gamma-ray signal in acquired gamma-ray data, $r_i$ corresponds to a particular sensitivity map for a gamma-ray sensing system, and $a_i$ corresponds to a gamma-ray distribution of desired gamma-ray signals without background gamma-ray noise. In other words, the detected gamma-ray signal may be expressed as a vector such as $\{s_1, s_2, \ldots s_m\}$, where m is the total number of sensor steps that the core sample of interest traverses from one end of a sensing region to the other end of the sensing region. Furthermore, a sensitivity map $r_i$ may be expressed as a vector, matrix, or series of coefficients, such as $\{r_1, r_2, \ldots, r_n\}$ that are measured using a baseline core sample, where n is the number of points of the sensitivity map. Likewise, gamma-ray distribution $a_i$ may also be expressed as a vector $\{a_1, a_2, \ldots, a_k\}$ at a total k points.

In some embodiments, a sensor resolution of a gamma-ray log is substantially the same as the resolution of the sensitivity map. As such, the number of sensor steps m may satisfy the expression, m≥k+n−1, to determine an optimized number of sensor steps. However, when m>k+n−1, the acquired gamma-ray data may include situations where the core sample of interest is outside a sensing region of the detector and therefore the acquired gamma-ray data only includes background noise at those sensor steps. Equation (1) may be further expressed in a matrix format using the following equation:

$$S = RA \qquad \text{Equation (2)}$$

where Equation (2) may be further expressed using the following equations:

$$S = [s_1 \; s_2 \; \cdots \; s_{k+n-1}]^T \qquad \text{Equation (3)}$$

$$R = \begin{bmatrix} r_1 & & & & & & \\ r_2 & r_1 & & & 0 & & \\ r_3 & r_2 & r_1 & & & & \\ & & \ddots & & & & \\ & & r_n & \cdots & r_3 & r_2 & r_1 \\ & & & & & \ddots & \\ & & & & r_n & r_{n-1} & r_{n-2} \\ & 0 & & & & r_n & r_{n-1} \\ & & & & & & r_n \end{bmatrix} \qquad \text{Equation (4)}$$

$$A = [a_1 \; a_2 \; \cdots \; a_k]^T \qquad \text{Equation (5)}$$

where the dimensions of S, R, and A may correspond to (k+n−1)×1, (k+n−1)×k, and k×1, respectively, and T may denote a vector transpose operation.

Using Equations (2)-(5), for example, a gamma-ray inversion process may be performed that obtains a gamma-ray log A from the acquired gamma-ray data S by solving Eq. (2). In some embodiments, for example, a gamma-ray inversion process includes a Least Squares fitting (LS) operation or singular value decomposition (SVD) operation. Other estimation techniques may also be used to suppress impacts of measurements with large errors (e.g., cases with outlier measurement values), such as an iterative reweighted least squares (IRLS) operation. In particular, an IRLS operation may determine a desired signal A from acquired gamma-ray data S by minimizing a misfit function, such as a misfit function expressed in the following equation:

$$\min_A \frac{1}{p} \|RA - S\|^p \qquad \text{Equation (6)}$$

where p may be a predefined constant with values in [1, 2]. Further, the impact of S on a solution of Equation (6) may vary with a selection of p. When p=2, Equation (6) may provide a least-squares solution, in which case the solution to Equation (6) may be an inversion of the averaged gamma-ray data (e.g., gamma-ray measurements that also include measurements with large errors). When p approaches 1, an IRLS operation may progressively rely more on the majority of acquired gamma-ray data. In a case of p=1, an IRLS operation may behave as a median filter. In this particular case, as long as the number of measurements with very large errors is less than half of the total measurements, the inversion from IRLS may be reliable. Thus, Equations (1)-(6) above may be used in one or more linear solvers and/or non-linear solvers to determine a desired gamma-ray signal within acquired gamma-ray data for a core sample of interest.

In Block 340, one or more geological properties are determined for a geological region using a gamma-ray log in accordance with one or more embodiments. Based on filtered gamma-ray data, for example, a reservoir simulator may determine whether one or more formations include shale content, clay content, or ash content. Likewise, the filtered gamma-ray data from a gamma-ray inversion process may be used to interpret one or more depositional environments (e.g., because potassium and uranium are found in varying quantities in different minerals and depositional environments). Likewise, a gamma-ray log may be used in connection with other well log data and/or core sample data to model a reservoir region.

Figure 6:
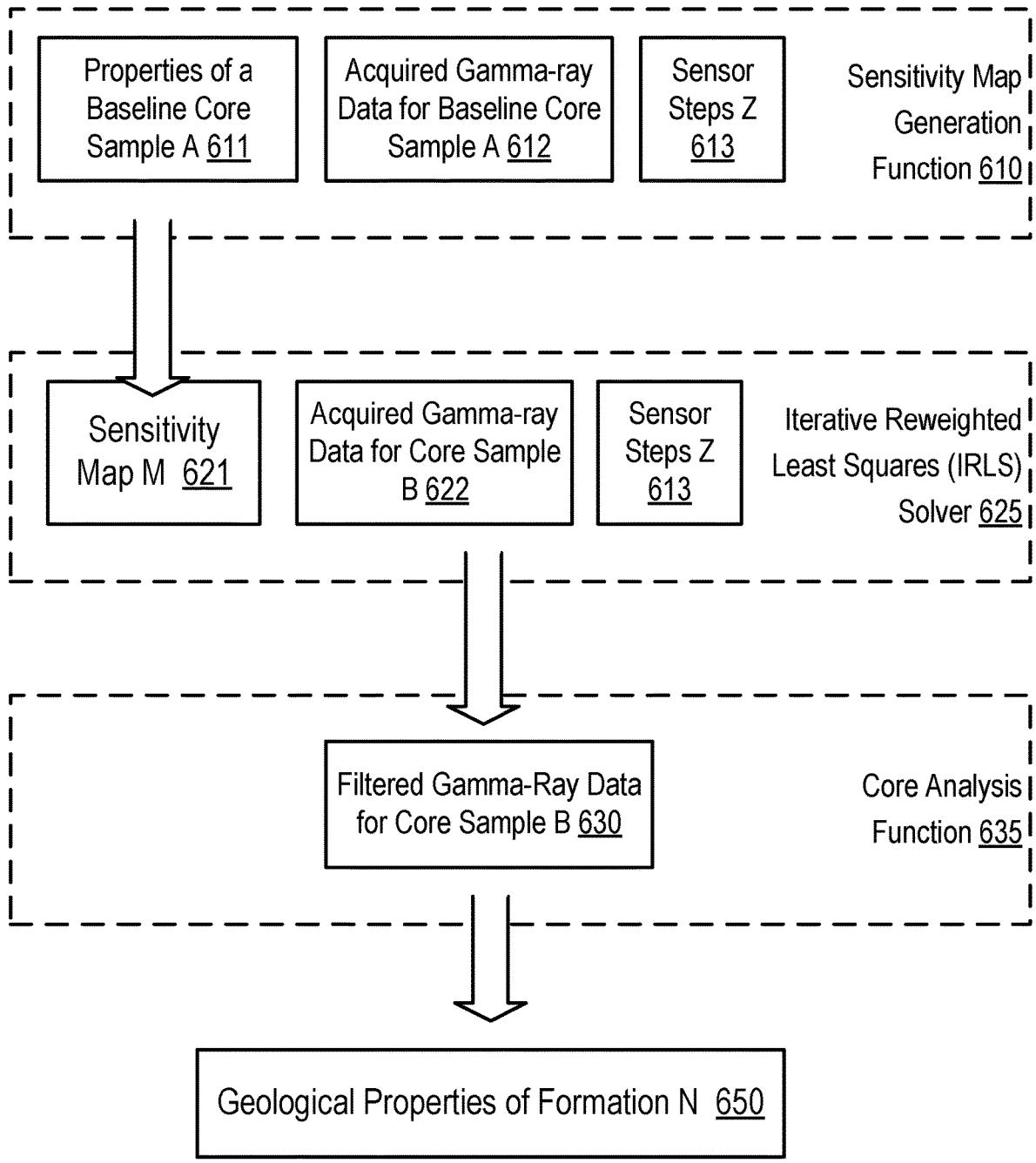

Turning to FIG. 6, FIG. 6 provides an example of generating and analyzing a gamma-ray log for a core sample in accordance with one or more embodiments. The following example is for explanatory purposes only and not intended to limit the scope of the disclosed technology. In FIG. 6, a gamma-ray sensing system (not shown) obtains various properties (611) of a baseline core sample A and acquired gamma-ray data (612) for the baseline core sample A at sensor steps Z (613). Using the properties (611) and the acquired gamma-ray data (612), the gamma-ray sensing system uses a sensitivity map generation function (610) to generate a sensitivity map M (621). After obtaining a sensitivity map M (621), the gamma-ray sensing system further obtains acquired gamma-ray data (622) at the same sensor steps Z (613) for a core sample B that is undergoing an analysis. The gamma-ray sensing system applies an iterative reweighted least squares solver (625) to the acquired gamma-ray data (622) using the sensitivity map M (621) to produce filtered gamma-ray data (630) for core sample B with removed background gamma-ray noise. Finally, the gamma-ray sensing system applies a core analysis function (635) to the filtered gamma-ray data (630) to determine various geological properties (650) of a formation N, where the core sample B was a specimen collected from the formation N.

Figure 7:
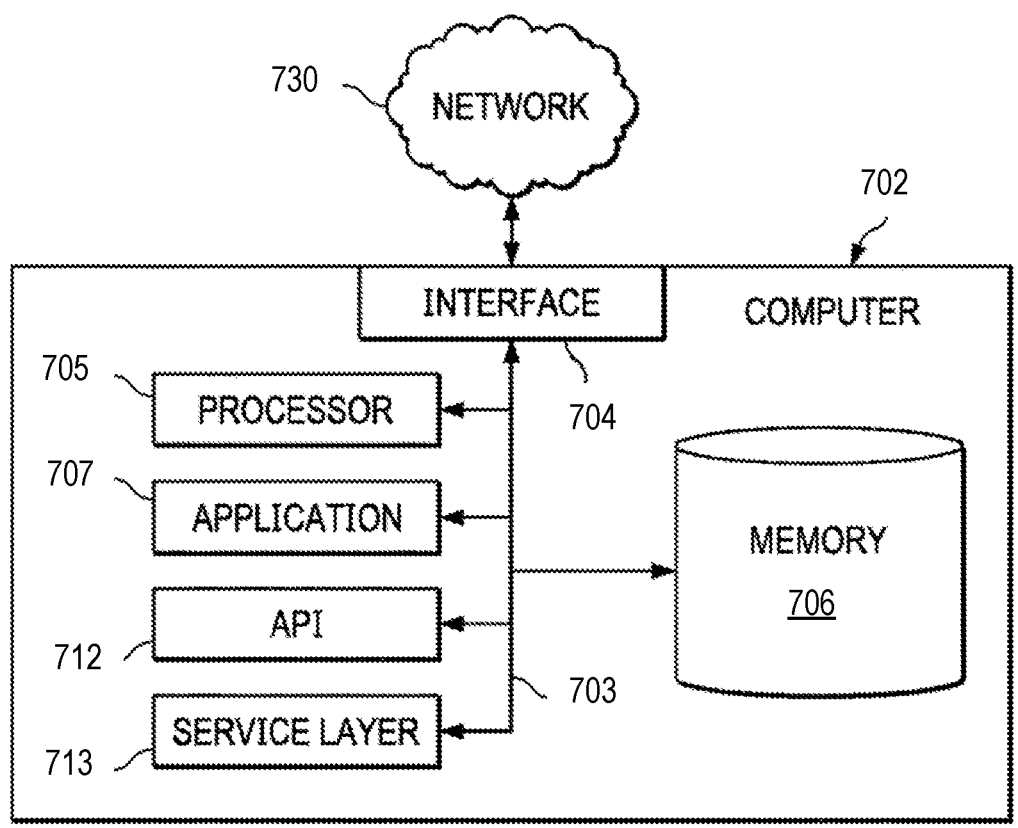
FIG. 7 shows a computer system in accordance with one or more embodiments.

Embodiments may be implemented on a computer system. FIG. 7 is a block diagram of a computer system (702) used to provide computational functionalities associated with described algorithms, methods, functions, processes, flows, and procedures as described in the instant disclosure, according to an implementation. The illustrated computer (702) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (702) may include a computer that includes an input device, such as a keypad, keyboard, touch screen, or other device that can accept user information, and an output device that conveys information associated with the operation of the computer (702), including digital data, visual, or audio information (or a combination of information), or a GUI.

The computer (702) can serve in a role as a client, network component, a server, a database or other persistency, or any other component (or a combination of roles) of a computer system for performing the subject matter described in the instant disclosure. The illustrated computer (702) is communicably coupled with a network (730). In some implementations, one or more components of the computer (702) may be configured to operate within environments, including cloud-computing-based, local, global, or other environment (or a combination of environments).

At a high level, the computer (702) is an electronic computing device operable to receive, transmit, process, store, or manage data and information associated with the described subject matter. According to some implementations, the computer (702) may also include or be communicably coupled with an application server, e-mail server, web server, caching server, streaming data server, business intelligence (BI) server, or other server (or a combination of servers).

The computer (702) can receive requests over network (730) from a client application (for example, executing on another computer (702)) and responding to the received requests by processing the said requests in an appropriate software application. In addition, requests may also be sent to the computer (702) from internal users (for example, from a command console or by other appropriate access method), external or third-parties, other automated applications, as well as any other appropriate entities, individuals, systems, or computers.

Each of the components of the computer (702) can communicate using a system bus (703). In some implementations, any or all of the components of the computer (702), both hardware or software (or a combination of hardware and software), may interface with each other or the interface (704) (or a combination of both) over the system bus (703) using an application programming interface (API) (712) or a service layer (713) (or a combination of the API (712) and service layer (713). The API (712) may include specifications for routines, data structures, and object classes. The API (712) may be either computer-language independent or dependent and refer to a complete interface, a single function, or even a set of APIs. The service layer (713) provides software services to the computer (702) or other components (whether or not illustrated) that are communicably coupled to the computer (702). The functionality of the computer (702) may be accessible for all service consumers using this service layer. Software services, such as those provided by the service layer (713), provide reusable, defined business functionalities through a defined interface. For example, the interface may be software written in JAVA, C++, or other suitable language providing data in extensible markup language (XML) format or other suitable format. While illustrated as an integrated component of the computer (702), alternative implementations may illustrate the API (712) or the service layer (713) as stand-alone components in relation to other components of the computer (702) or other components (whether or not illustrated) that are communicably coupled to the computer (702). Moreover, any or all parts of the API (712) or the service layer (713) may be implemented as child or sub-modules of another software module, enterprise application, or hardware module without departing from the scope of this disclosure.

The computer (702) includes an interface (704). Although illustrated as a single interface (704) in FIG. 7, two or more interfaces (704) may be used according to particular needs, desires, or particular implementations of the computer (702). The interface (704) is used by the computer (702) for communicating with other systems in a distributed environment that are connected to the network (730). Generally, the interface (704 includes logic encoded in software or hardware (or a combination of software and hardware) and operable to communicate with the network (730). More specifically, the interface (704) may include software supporting one or more communication protocols associated with communications such that the network (730) or interface's hardware is operable to communicate physical signals within and outside of the illustrated computer (702).

The computer (702) includes at least one computer processor (705). Although illustrated as a single computer processor (705) in FIG. 7, two or more processors may be used according to particular needs, desires, or particular implementations of the computer (702). Generally, the computer processor (705) executes instructions and manipulates data to perform the operations of the computer (702) and any algorithms, methods, functions, processes, flows, and procedures as described in the instant disclosure.

The computer (702) also includes a memory (706) that holds data for the computer (702) or other components (or a combination of both) that can be connected to the network (730). For example, memory (706) can be a database storing data consistent with this disclosure. Although illustrated as a single memory (706) in FIG. 7, two or more memories may be used according to particular needs, desires, or particular implementations of the computer (702) and the described functionality. While memory (706) is illustrated as an integral component of the computer (702), in alternative implementations, memory (706) can be external to the computer (702).

The application (707) is an algorithmic software engine providing functionality according to particular needs, desires, or particular implementations of the computer (702), particularly with respect to functionality described in this disclosure. For example, application (707) can serve as one or more components, modules, applications, etc. Further, although illustrated as a single application (707), the application (707) may be implemented as multiple applications (707) on the computer (702). In addition, although illustrated as integral to the computer (702), in alternative implementations, the application (707) can be external to the computer (702).

There may be any number of computers (702) associated with, or external to, a computer system containing computer (702), each computer (702) communicating over network (730). Further, the term "client," "user," and other appropriate terminology may be used interchangeably as appropriate without departing from the scope of this disclosure. Moreover, this disclosure contemplates that many users may use one computer (702), or that one user may use multiple computers (702).

In some embodiments, the computer (702) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed:

1. A method, comprising:
   obtaining, by a computer processor and using a gamma-ray sensing system comprising a gamma-ray detector and a sensing region, first acquired gamma-ray data regarding a first core sample,
      wherein the first core sample is analyzed by the gamma-ray sensing system at a plurality of periodic intervals in the sensing region using a controlled sampling motion comprising a plurality of sensor steps, and
      wherein a respective sensor step among the plurality of sensor steps defines a predetermined change in distance of the first core sample in the sensing region with respect to the gamma-ray detector;
   determining, by the computer processor, a sensitivity map based on the first acquired gamma-ray data and comprising a plurality of weighted coefficients, wherein a respective weighted coefficient among the plurality of weighted coefficients correspond to the respective sensor step;
   obtaining, by the computer processor and using the gamma-ray detector, second acquired gamma-ray data regarding a second core sample at the plurality of sensor steps wherein the respective weighted coefficient determines a filtered gamma-ray signal for a portion of the second acquired gamma-ray data at the respective sensor step; and
   generating, by the computer processor, a gamma-ray log using the sensitivity map and a gamma-ray inversion process.

2. The method of claim 1, further comprising:
   determining one or more geological properties for a geological region of interest using the gamma-ray log, wherein the geological region of interest corresponds to a predetermined formation, and
   wherein the second core sample is acquired from a well in the predetermined formation.

3. The method of claim 2,
   wherein the one or more geological properties corresponds to an amount of shale content in the geological region of interest.

4. The method of claim 1, further comprising:
   obtaining a nonlinear solver that performs an iterative reweighted least squares (IRLS) operation, wherein the gamma-ray inversion process uses the nonlinear solver to minimize a predetermined misfit function.

5. The method of claim 1,
wherein the first core sample is a baseline core sample.

6. The method of claim 1,
wherein the gamma-ray detector is moved at the plurality of sensor steps along a first axis of the first core sample, and
wherein the first core sample is longer with respect to the first axis than a second axis that is perpendicular to the first axis.

7. The method of claim 1,
wherein the second core sample is acquired from a well in a coring operation using a core bit, a core barrel, and a core catcher.

8. The method of claim 1,
wherein the gamma-ray detector is a passive detector in a gamma-ray system without an active gamma-ray source.

9. A system, comprising:
a gamma-ray detector configured to detect a plurality of gamma rays from a sensing region; and
a host device comprising a computer processor, wherein the host device is coupled to the gamma-ray detector, the host device being configured to perform a method comprising:
  obtaining, using the gamma-ray detector, first acquired gamma-ray data regarding a first core sample,
    wherein the first core sample is analyzed at a plurality of periodic intervals in the sensing region using a controlled sampling motion comprising a plurality of sensor steps, and
    wherein a respective sensor step among the plurality of sensor steps defines a predetermined change in distance of the first core sample in the sensing region with respect to the gamma-ray detector;
  determining a sensitivity map based on the first acquired gamma-ray data and comprising a plurality of weighted coefficients, wherein a respective weighted coefficient among the plurality of weighted coefficients correspond to the respective sensor step;
  obtaining, using the gamma-ray detector, second acquired gamma-ray data regarding a second core sample at the plurality of sensor steps, wherein the respective weighted coefficient determines a filtered gamma-ray signal for a portion of the second acquired gamma-ray data at the respective sensor step; and
  generating a gamma-ray log using the sensitivity map and a gamma-ray inversion process.

10. The system of claim 9, wherein the host device further comprises functionality for:
determining one or more geological properties for a geological region of interest using the gamma-ray log,
wherein the geological region of interest corresponds to a predetermined formation, and
wherein the second core sample is acquired from a well in the predetermined formation.

11. The system of claim 9, wherein the host device further comprises functionality for:
obtaining a nonlinear solver that performs an iterative reweighted least squares (IRLS) operation,
wherein the gamma-ray inversion process uses the nonlinear solver to minimize a predetermined misfit function.

12. The system of claim 9,
wherein the gamma-ray detector is moved at the plurality of sensor steps along a first axis of the first core sample, and
wherein the first core sample is longer with respect to the first axis than a second axis that is perpendicular to the first axis.

13. The system of claim 9, further comprising:
a logging system coupled to a wellbore, wherein the logging system comprises a coring tool,
wherein the second core sample is acquired from a well in a coring operation using the coring tool.

14. The system of claim 9,
wherein the gamma-ray detector is a passive detector in a gamma-ray system without an active gamma-ray source.

15. A non-transitory computer readable medium storing instructions executable by a computer processor, the instructions comprising functionality for:
obtaining, from a gamma-ray sensing system comprising a gamma-ray detector and a sensing region, first acquired gamma-ray data regarding a first core sample,
  wherein the first core sample is analyzed by the gamma-ray sensing system at a plurality of periodic intervals in the sensing region using a controlled sampling motion comprising a plurality of sensor steps, and
  wherein a respective sensor step among the plurality of sensor steps defines a predetermined change in distance of the first core sample in the sensing region with respect to the gamma-ray detector;
determining a sensitivity map based on the first acquired gamma-ray data and comprising a plurality of weighted coefficients, wherein a respective weighted coefficient among the plurality of weighted coefficients correspond to the respective sensor step;
obtaining, from the gamma-ray detector, second acquired gamma-ray data regarding a second core sample at the plurality of sensor steps, wherein the respective weighted coefficient determines a filtered gamma-ray signal for a portion of the second acquired gamma-ray data at the respective sensor step; and
generating a gamma-ray log using the sensitivity map and a gamma-ray inversion process.

16. The non-transitory computer readable medium of claim 15, the instructions further comprising functionality for:
determining one or more geological properties for a geological region of interest using the gamma-ray log,
wherein the geological region of interest corresponds to a predetermined formation, and
wherein the second core sample is acquired from a well in the predetermined formation.

17. The non-transitory computer readable medium of claim 15, the instructions further comprising functionality for:
obtaining a nonlinear solver that performs an iterative reweighted least squares (IRLS) operation,
wherein the gamma-ray inversion process uses the nonlinear solver to minimize a predetermined misfit function.

* * * * *